(12) United States Patent
Reuterholt et al.

(10) Patent No.: US 9,285,257 B2
(45) Date of Patent: Mar. 15, 2016

(54) GAS METER FOR ULTRASOUND MEASUREMENTS IN A BREATHING APPARATUS HAVING SELF-DRAINING CONDUIT ARRANGEMENT

(75) Inventors: Johan Reuterholt, Bålsta (SE); Lars Danielsen, Hässelby (SE)

(73) Assignee: Maquet Critical Care AB, Solna (SE)

( * ) Notice: Subject to any disclaimer, the term of this patent is extended or adjusted under 35 U.S.C. 154(b) by 706 days.

(21) Appl. No.: 13/516,151

(22) PCT Filed: Dec. 18, 2009

(86) PCT No.: PCT/SE2009/051468
§ 371 (c)(1),
(2), (4) Date: Aug. 23, 2012

(87) PCT Pub. No.: WO2011/075030
PCT Pub. Date: Jun. 23, 2011

(65) Prior Publication Data
US 2013/0032152 A1 Feb. 7, 2013

(51) Int. Cl.
*G01F 1/66* (2006.01)
*A61B 5/087* (2006.01)
*A61M 16/00* (2006.01)
*A61M 16/10* (2006.01)

(52) U.S. Cl.
CPC ............... *G01F 1/662* (2013.01); *A61B 5/087* (2013.01); *A61M 2016/0033* (2013.01); *A61M 2016/102* (2013.01); *A61M 2205/3375* (2013.01)

(58) Field of Classification Search
None
See application file for complete search history.

(56) References Cited

U.S. PATENT DOCUMENTS

| | | | |
|---|---|---|---|
| 4,004,461 A * | 1/1977 | Lynnworth | 73/861.27 |
| 4,425,804 A * | 1/1984 | Mount et al. | 73/861.28 |
| 4,425,805 A | 1/1984 | Ogura et al. | |
| 4,735,097 A * | 4/1988 | Lynnworth | G01F 1/662 73/290 V |
| 4,823,612 A | 4/1989 | Ichino | |
| 4,932,269 A | 6/1990 | Cammarata, III et al. | |
| 5,893,642 A * | 4/1999 | Hewitt et al. | 366/338 |
| 6,330,831 B1 * | 12/2001 | Lynnworth et al. | 73/861.28 |
| 2008/0209984 A1 * | 9/2008 | Yamada | 73/31.05 |

FOREIGN PATENT DOCUMENTS

| | | |
|---|---|---|
| EP | 0 078 381 | 5/1983 |
| JP | 11051723 A | 2/1999 |
| WO | WO 96/13701 | 5/1996 |
| WO | WO-98/55838 | 12/1998 |
| WO | WO 98/55838 | 12/1998 |

\* cited by examiner

*Primary Examiner* — Harshad R Patel
(74) *Attorney, Agent, or Firm* — Schiff Hardin LLP

(57) ABSTRACT

A gas meter for ultrasound measurements in a breathing apparatus has a gas conduit having an inner wall defining an inlet of the gas conduit and an outlet in a second end of the gas conduit, and an ultrasound transducer arrangement configured to measure the speed of sound in a gas flowing through a part of said gas conduit forming a measurement chamber. The gas meter has a self-draining design to prevent condensation water and other liquids from negatively affecting the ultrasound measurements. To this end, at least a lower surface of the inner wall of the gas conduit is inclined downwardly relative to the horizontal plane in the longitudinal direction of the gas conduit, at both sides of the measurement chamber causing condensation water to be pulled away from the measurement chamber by gravity.

13 Claims, 3 Drawing Sheets

GAS METER FOR ULTRASOUND MEASUREMENTS IN A BREATHING APPARATUS HAVING SELF-DRAINING CONDUIT ARRANGEMENT

BACKGROUND OF THE INVENTION

1. Field of the Invention

The present invention relates to a gas meter for ultrasound measurements in a breathing apparatus of the type having a gas conduit with an inner wall that defines an inlet at a first end of the gas conduit and outlet in a second end of the gas conduit, and having an ultrasound transducer arrangement that measures the speed of sound in a gas flowing through a part of the gas conduit that forms a measurement chamber.

2. Description of the Prior Art

Ultrasonic gas meters for measuring the flow or the composition of a gas are well known in the art and commonly used in breathing apparatuses, such as ventilators and anaesthesia machines. Such a gas meter typically operates by determining the time of flight for an acoustic (ultrasonic) pulse transmitted through the gas flowing through a gas conduit of the breathing apparatus. The time of flight may then be used to determine the flow of the gas if the gas composition is known, or vice versa.

In order to accurately determine the time of flight of the acoustic pulses it is important to avoid the presence of condensation water or other liquids in the immediate surroundings of the acoustic transducers and in the part of the gas conduit through which the acoustic pulses are transmitted, hereinafter referred to as the measurement chamber.

One problem which may occur if condensation water accumulates in the measurement chamber is that it may reflect the acoustic pulses such that the travel distance and hence the time of flight for the pulses is changed. This problem mainly arises in single-transducer arrangements in which a single ultrasonic transducer mounted on one side of the gas conduit is used both to transmit acoustic pulses through the gas and to receive the pulses after being reflected by the inner wall on the opposite side of the gas conduit, or a reflector element arranged on the opposite side of the gas conduit. In such a single-transducer arrangement, condensation water on the inner wall or reflector element may severely deteriorate the accuracy in the determination of gas flow or composition.

Another problem may occur if condensation water is gathered around the ultrasonic transducer itself. Typically, the ultrasonic transducer is mounted in a transducer housing protruding from the gas conduit. If condensation water penetrates the air gap normally existing between the transducer and the transducer housing, the acoustic pulses may propagate through the material of the transducer housing and further on through the gas conduit, giving rise to various undesired effects. This problem mainly arises in double-transducer arrangements in which two ultrasonic transducers, one acting as a transmitter and the other as a receiver, are arranged on opposite sides of the gas conduit. If condensation water penetrates the air gap in both transducer housings, the acoustic pulses may propagate between the transducers via the transducer housings and the gas conduit instead of through the gas. Such a "short-circuiting" of the ultrasound transducers will, of course, result in erroneous time of flight measurements.

Several solutions have been proposed in order to avoid accumulation of condensation water in ultrasonic gas meters.

European patent application EP 0078381 A2 discloses an ultrasonic air flow transducer arrangement for high humidity environments. The transducers are mounted in transducer housings which are heated by heating means in order to maintain the gas inside the housings at a temperature higher than ambient temperature to prevent moisture from forming therein. The arrangement further comprises water absorbing material to prevent condensation water from entering the transducers and affecting gas measurements.

International patent application WO 96/13701 discloses an ultrasonic gas meter which is designed to prevent liquid accumulation in the transducer housings. This is achieved by draining ducts extending generally horizontally between the transducer cavities defined by the transducer housing and the bore through which the gas flows, or vertically from the cavities to the outside of the transducer housing to permit accumulated liquid to be drained by gravity.

Japanese patent application JP 11051723 A discloses an ultrasonic gas meter in which the longitudinal direction of the gas conduit, or gas transmission passage, is inclined to the horizontal direction to keep the inner wall of the gas conduit clean. In this way, impurities are washed away by condensation water flowing down the inner wall of the gas conduit.

SUMMARY OF THE INVENTION

It is object of the present invention to improve the reliability of ultrasound measurements on a gas in a breathing apparatus.

This object is achieved by a gas meter for ultrasound measurements in a breathing apparatus, having a gas conduit having an inner wall defining an inlet in a first end of the gas conduit and an outlet in a second end of the gas conduit, and an ultrasound transducer arrangement configured to measure the speed of sound in a gas flowing through a part of the gas conduit forming a measurement chamber. The gas meter is designed such that at least a lower surface of the inner wall is inclined downwardly relative to the horizontal plane in the longitudinal direction of the gas conduit, at both sides of the measurement chamber, so that condensation water will be pulled away from the measurement chamber by gravity.

Since the at least lower surface of the inner wall of the gas conduit is inclined so as to form a downhill slope from the measurement chamber toward the inlet and from the measurement chamber toward the outlet, condensation water or liquid springing from humidified gas will be forced toward the inlet and outlet of the gas conduit, away from the measurement chamber and the ultrasound transducer arrangement. Thus, the invention presents a gas meter having a self-draining design.

From the above it should be appreciated that the measurement chamber of the gas meter is the part of the gas conduit in which ultrasound measurements are performed, i.e. the volume of the gas conduit traversed by ultrasonic pulses transmitted and received by the ultrasound transducer arrangement. In general terms, the invention provides a gas meter in which the gas conduit is curved along its longitudinal direction and in which the measurement chamber is located at the highest point of the gas conduit such that condensation water and other liquids will be pulled away from there by gravity.

Additionally, also an upper surface of the inner wall of the gas conduit may be inclined downwardly relative to the horizontal plane in the longitudinal direction of the gas conduit, at both sides of the measurement chamber, such that also condensation water formed on the "ceiling" of the gas conduit will be pulled away from the measurement chamber and the ultrasound transducer arrangement by gravity.

The inclined surface (or surfaces) of the inner wall of the gas conduit may, for example, be upwardly convex relative to the horizontal plane in the longitudinal direction of the gas conduit. However, it (or they) may also have a substantially constant, positive slope from the inlet to the measurement chamber and a substantially constant, negative slope from the measurement chamber to the outlet. The latter hence resulting in a surface having an inverted V-shape in the longitudinal direction of the gas conduit.

In one embodiment, the gas conduit is a slightly bent, cylindrical conduit of uniform thickness which is upwardly convex relative to the horizontal plane. In another embodiment, the lower portion of the inner wall of the gas conduit has the above described inverted V-shape whereas the upper surface of the inner wall (i.e. the "ceiling" of the gas conduit) is substantially horizontal. This is advantageous in that the area of the inner cross section of the gas conduit will vary along the longitudinal direction of the gas conduit and assume its smallest value within the measurement chamber. Thus, the gas conduit is shaped such that the at least one surface that is inclined relative to the horizontal plane to give the self-draining effect simultaneously serves as a constriction of the flow channel. This has the effect of increasing the velocity of the gas within the measurement chamber, which in turn increases the accuracy in the ultrasound measurements.

The above gas conduit design may be realized by providing the gas conduit with substantially planar inner walls constituting top, bottom and side walls of the gas conduit. The top wall may form a substantially horizontal, planar ceiling of the gas conduit whereas the bottom wall may form a planar floor having an inverted V-shape with its highest point within the measurement chamber. To further increase the velocity of the gas in the measurement chamber, one or both of the side walls of the gas conduit may also be slightly V-shaped with the base of the V pointing into the measurement chamber of the gas conduit.

Preferably, the inclined surface or surfaces of the inner wall of the gas conduit are non-horizontal in the longitudinal direction of the gas conduit also within the measurement chamber.

The first and the second ends of the gas conduit are each preferably provided with a connection configured to allow the gas conduit to be connected inline with a gas flow path, such as a gas flow path of a breathing apparatus conveying inspiration gas and/or expiration gas to/from a patient. Preferably, the first and the second ends of the gas conduit are horizontally aligned to allow the gas conduit of the gas meter to be connected inline with a substantially horizontal gas flow path, and the connections are configured to allow the gas conduit to be connected in between two horizontal and longitudinally aligned gas conduits forming a part of a gas flow path.

The ultrasound transducer arrangement of the gas meter may be a single-transducer arrangement comprising a single ultrasound transducer serving as a combined transmitter/receiver, or a double-transducer arrangement that includes one transducer serving as an ultrasound transmitter and another transducer serving as an ultrasound receiver.

The at least one transducer may be arranged in a transducer housing protruding substantially horizontally from the gas conduit. The transducer housing has an inner wall that forms a transducer cavity having a closed end at which the transducer is arranged and an open end defining an opening into the measurement chamber of the gas conduit. The transducer is arranged to transmit and/or receive ultrasonic pulses through the opening.

Preferably, at least a lower surface of the inner wall of the transducer housing is inclined downwardly relative to the horizontal plane from the closed end of the transducer cavity towards the open end, such that condensation water will be pulled out of the transducer cavity by gravity. If condensation water were to penetrate the measurement chamber in spite of the proposed self-draining gas meter design, the non-horizontal inner wall of the transducer housing prevents the water from penetrating the transducer cavity, thereby minimizing the risk of transducer short-circuiting.

To further minimize the risk of condensation water penetrating the transducer cavity and filling the air gap normally existing between the transducer and the transducer housing, the gas meter may include a heat generator, such as a resistive heating film, arranged to locally heat the area around the or each transducer.

The gas meter is intended for use in a breathing apparatus, such as a ventilator or anaesthesia machine, comprising a tubing system for supplying gas to and from a patient. Preferably, the gas meter is a stand-alone device arranged to be detachably connected inline with the tubing system of a breathing apparatus to form a part thereof. Additionally, the gas meter may form a permanent part of the tubing system of a breathing apparatus. The disclosed self-draining gas meter design is particularly advantageous when the gas meter is used in a part of a breathing apparatus tubing system conveying humidified gas exhaled by the patient.

DESCRIPTION OF THE PREFERRED EMBODIMENTS

Figure 1A:
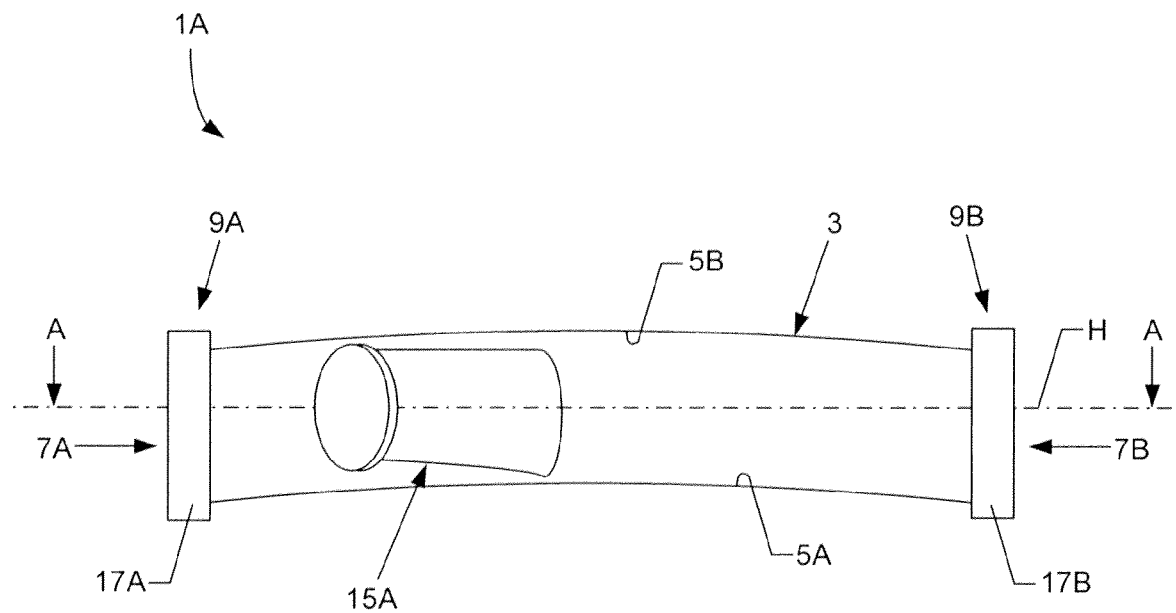
FIG. 1A illustrates a side view of a gas meter according to an exemplary embodiment of the invention.
Figure 2A:
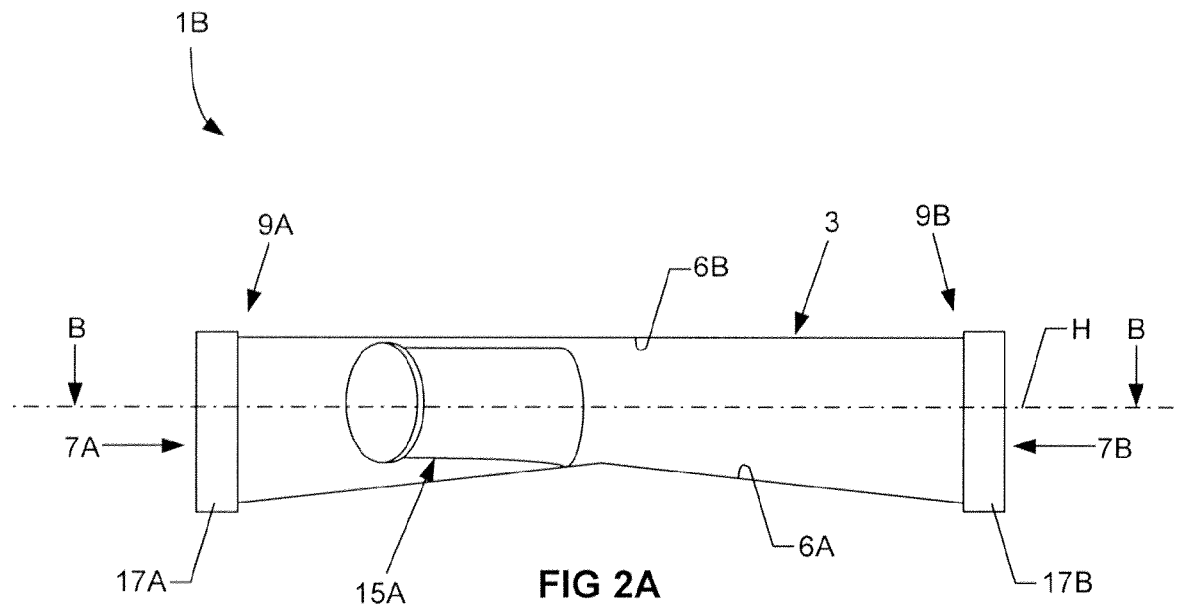
FIG. 2A illustrates a side view of a gas meter according to another exemplary embodiment of the invention.

FIG. 1A illustrates a side view of a gas meter 1A for ultrasound measurements in a breathing apparatus according to a first embodiment of the invention. The gas meter 1A has a gas conduit 3 having an inner wall defining an inlet 7A in a first end 9A of the gas conduit and an outlet 7B in a second end 9B of the gas conduit. The inner wall has a lower inner wall surface 5A and an upper inner wall surface 5B. In this embodiment, the gas conduit 3 is preferably a cylindrical conduit of uniform thickness which is upwardly convex relative to the horizontal plane, illustrated by the dash-dotted line denoted H. Of course, the gas conduit 3 does not have to be a cylindrical conduit having a circular cross section. For example, the gas conduit 3 could be a quadrilateral tube having a rectangular cross section. It should be appreciated that any spatial term used herein, such as "upwardly", refers to the gas meter when orientated as shown in FIGS. 1A and 2A of the drawings, which is the intended orientation of the gas meter during use.

Figure 1B:
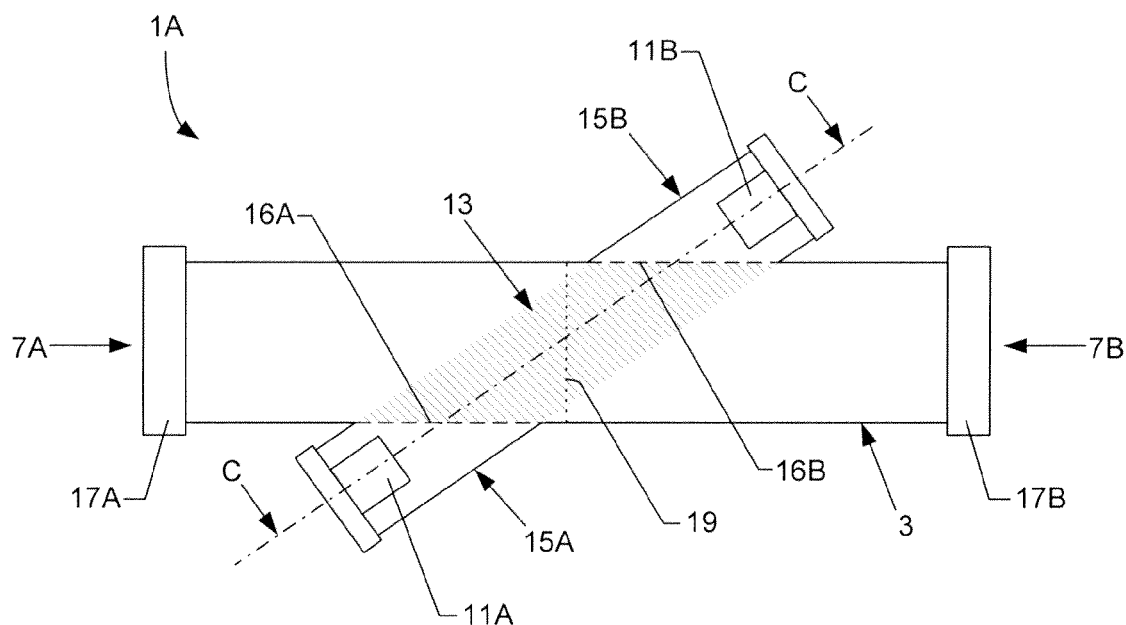
FIG. 1B illustrates a cross-sectional view of the gas meter illustrated in FIG. 1A.

With reference to FIG. 1B which illustrates a cross-sectional view of the gas meter 1A taken along the line A-A in FIG. 1A, the gas meter 1A further includes an ultrasound transducer arrangement configured to measure the speed of sound in a gas flowing through a part of the gas conduit 3 forming a measurement chamber 13. The part of the gas conduit 3 forming the measurement chamber 13 is indicated with dashed lines in FIG. 1B. In this exemplary embodiment, the ultrasound transducer arrangement comprises two ultrasound transducers 11A, 11B, one serving as an ultrasound transmitter and one serving as an ultrasound receiver during each measurement. The ultrasound transducers 11A, 11B may be configured to change roles such that the ultrasound transducer serving as an ultrasound receiver during a measurement serves as an ultrasound transmitter during another measurement, and vice versa. The ultrasound transducers 11A, 11B are arranged on opposite sides of the gas conduit 3, substantially horizontally aligned (i.e. located in the same horizontal plane) and arranged at an angle to the gas conduit 3 such that ultrasonic pulses are transmitted in a non-perpendicular direction to a flow of gas through the gas conduit 3. During use, the ultrasound transducers 11A, 11B are connected to an analysis unit (not shown), such as a control unit of a breathing apparatus, which analysis unit determines the flow or the composition of the gas flowing through the gas conduit 3 based on the time of flight of ultrasonic pulses transmitted between the ultrasound transducers 11A, 11B, through the gas in the measurement chamber 13.

The ultrasound transducers 11A, 11B are arranged in a respective transducer housing 15A, 15B protruding substantially horizontally from the gas conduit 3. Each transducer housing 15A, 15B has an inner wall which forms a transducer cavity having a closed end at which the transducer 11A, 11B is arranged and an open end defining an opening 16A, 16B into the measurement chamber 13 of the gas conduit 3, through which opening the transducer is arranged to transmit and/or receive the ultrasonic pulses. The transducer housings 15A, 15B, which are preferably integrally formed with the gas conduit 3, will be described in more detail later on with reference to FIG. 3.

Furthermore, the gas meter 1A is seen to comprise connection means 17A, 17B provided at the first 9A and second 9B ends of the gas conduit 3. The connection means 17A, 17B are configured to allow the gas conduit 3 to be connected inline with a gas flow path in a breathing apparatus, conveying a gas that is to be analyzed by the gas meter 1A. To this end, the connection means 17A, 17B are preferably adapted to allow the first 9A and second 9B end of the gas conduit 3 to be connected to standard breathing apparatus tubing. The first 9A and second 9B ends of the gas conduit 3 are horizontally aligned, and the connection means 17A, 17B are configured to allow the gas conduit 3 to be connected in between two horizontal and longitudinally aligned gas conduits forming a part of the breathing apparatus tubing.

The upwardly convex shape of the gas conduit 3 makes the inner wall of the gas conduit 3 incline downwardly relative to the horizontal plane, H, in the longitudinal direction of the gas conduit, at both sides of the measurement chamber 13. Thereby, condensation water and any other liquid which may form inside the gas conduit 3 due to humidified gas flowing therein during use of the gas meter 1A will be pulled away from the measurement chamber 13 by gravity and prevent water from entering the measurement chamber 13 and the transducer cavities communicating with the measurement chamber 13 through the openings 16A, 16B. In this embodiment, the entire gas conduit 3 is inclined downwardly on both sides of the measurement chamber 13. However, it should be appreciated that the self-draining effect, at least to a certain extent, is achieved as long as at least the lower inner wall surface 5A, i.e. the surface of the inner wall forming a "floor" of the gas conduit 3 during intended use of the gas meter 1A, forms a downward slope from the measurement chamber 13 towards the inlet 9A, and from the measurement chamber 13 toward the outlet 9B.

Preferably, to prevent condensation water formed in the measurement chamber 13 to stay there, at least the lower inner wall surface 5A is non-horizontal also within the measurement chamber 13. The dotted line 19 in FIG. 1B illustrates the highest point of the lower inner wall surface 5A of the gas conduit 3. Preferably, this point 19 should, at least partly, lie inside the measurement chamber 13. Even more preferably, at least the lower inner wall surface 5A of the gas conduit 3 is arranged such that its highest point 19 lies at least partly inside the measurement chamber 13, and such that it inclines downwardly all the way from the highest point 19 to the inlet 9A and all the way from the highest point 19 to the outlet 9B.

FIG. 2A illustrates a side view of a gas meter 1B for ultrasound measurements in a breathing apparatus according to a second embodiment of the invention.

Figure 2B:
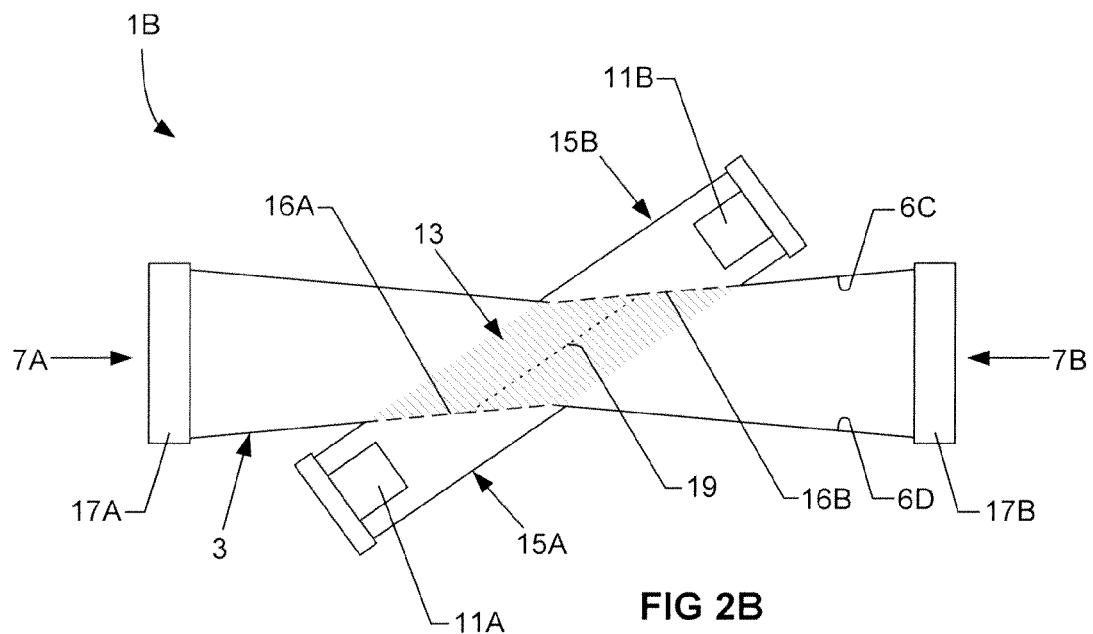
FIG. 2B illustrates a cross-sectional view of the gas meter illustrated in FIG. 2A.

With reference to FIG. 2B, which illustrates a cross-sectional view of the gas meter 1B taken along the line B-B in FIG. 2A, the gas conduit 3 is shown as having four substantially planar inner wall portions 6A-6D, constituting bottom, top, and side walls, respectively, of the gas conduit 3. The lower inner wall surface 6A of the gas conduit 3 has a substantially constant, positive slope from the inlet 7A to the measurement chamber 13, and a substantially constant, negative slope from the measurement chamber 13 to the outlet 7B. Thus, the lower inner wall surface 6A of the gas conduit 3 has an inverted V-shape in the longitudinal direction of the gas conduit 3, with the base of the inverted 'V' being located within the measurement chamber 13. The dotted line 19 in FIG. 2B illustrates the highest point of the lower inner wall surface 6A of the gas conduit 3, which, in this embodiment, forms a ridge of the lower inner wall surface 6A, running through the measurement chamber 13 along the acoustic path of the ultrasonic pulses transmitted between the ultrasound transducers 11A, 11B.

The upper inner wall surface 6B of the gas conduit 3 is substantially horizontal in the longitudinal direction of the gas conduit 3. Thus, the inverted V-shape of the lower inner wall surface 6A makes the cross-sectional area of the gas conduit 3 smaller inside the measurement chamber 13 than outside the measurement chamber. Besides providing a self-draining effect by forcing condensation water and other liquids to be pulled away from the measurement chamber 13 by gravity, the lower inner wall surface 6A hence also forms a constriction of the flow channel, inside the measurement chamber 13. This is advantageous in that the velocity of a gas streaming through the gas conduit 3 will increase within the measurement chamber 19, which in turn increases the accuracy in ultrasound measurements. As seen in FIG. 2B, to further increase the velocity of the gas through the measurement chamber 13, also the planar inner wall surfaces 6C and 6D, which form side walls of the gas conduit 3, are slightly V-shaped with the base of the V pointing into the measurement chamber 13 of the gas conduit 3.

Figure 3:
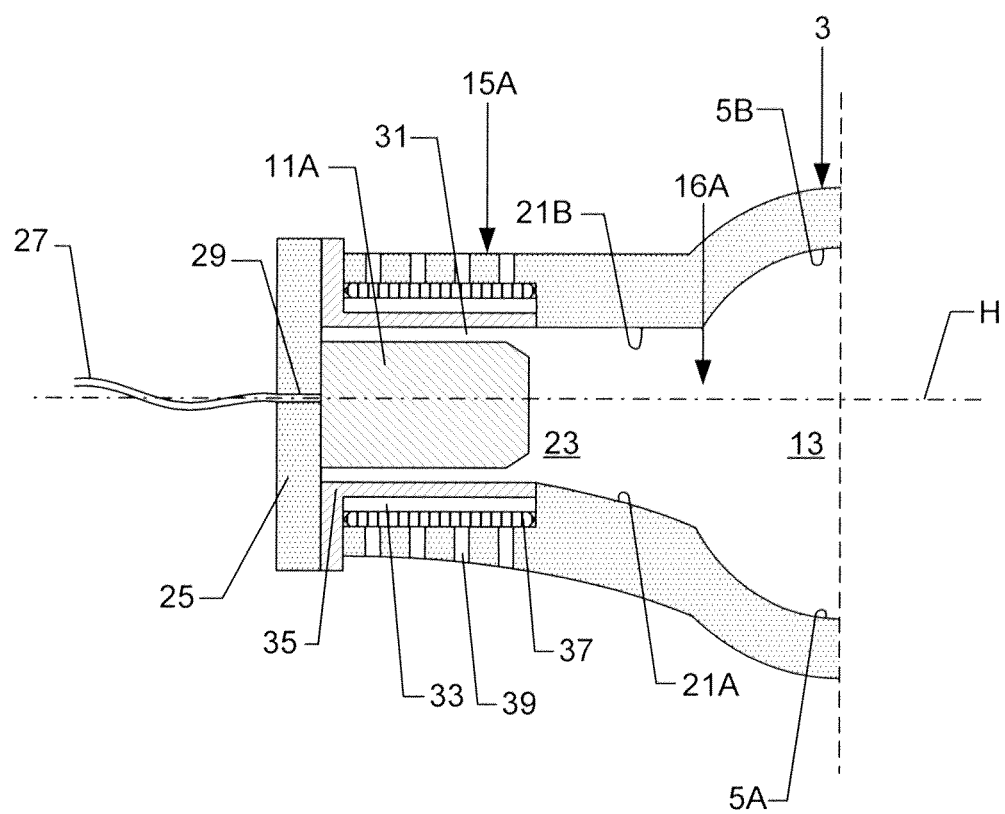
FIG. 3 illustrates a cross-sectional view of a transducer housing of a gas meter according to an exemplary embodiment of the invention.

FIG. 3 illustrates a more detailed view of a transducer housing 15A according to an exemplary embodiment of the invention. The drawing is a schematic view of a cross section of the transducer housing 15A and half the gas conduit 3, taken along the line C-C in FIG. 1B.

The transducer housing 15A comprises an inner wall which forms a transducer cavity 23 having a closed end at which the transducer 11A is arranged, and an open end defining an opening 16A into the measurement chamber 13 of the gas conduit 3. The transducer 11A is arranged to transmit and/or receive ultrasonic pulses to/from the opposite transducer 16B (see FIG. 1B) through the opening 16A. In this exemplary embodiment, the transducer housing 15A is substantially cylindrical and has a substantially circular cross section.

The transducer 11A is preferably detachably mounted in the transducer cavity 23. In this embodiment, the transducer 11A is attached to a plate 25 which serves as an end cap of the transducer housing 16A and seals the transducer cavity 23 when inserting the transducer 11A. The transducer 11A is connected to an analysis unit (not shown), such as a control unit of a breathing apparatus, via a wire 27 running through a bore 29 in the plate 25. The element constituted by the plate 25 and the transducer 11A may for example be detachably maintained in the desired position by spring clamps (not shown) clamping it to the transducer housing 16A.

The lower surface 21A of the inner wall of the transducer housing 15A is, in this embodiment, inclined upwardly relative to the horizontal plane, illustrated by the dash-dotted line denoted H, from the open end of the transducer cavity 23 (i.e. from the opening 16A) toward the closed end of the transducer cavity 23 at which the transducer 11A is arranged. Thereby, condensation water and other liquids which might form inside the measurement chamber 13 in spite of the self-draining design of the gas meter is prevented from penetrating the transducer cavity 23 and accumulate in air gaps 31 surrounding the transducer 11A. By preventing liquid from accumulating in the air gap 31, the risk of transducer short-circuiting is minimized.

Although being substantially horizontal in this exemplary embodiment, it should be appreciated that also the upper surface 21B of the inner wall of the transducer housing 15A may be inclined upwardly relative to the horizontal plane, from the open end of the transducer cavity 23 towards the closed end. Thus, it should be understood that the upper surface 21B of the transducer housing 15A may, in another embodiment, be formed the way the lower surface 21A is formed in embodiment illustrated in FIG. 3.

In addition to or instead of the inclined surface 21A of the transducer housing 15A, the transducer housing 15A may comprise one or several bores and/or channels or troughs (not shown) through which condensation water may be guided away from the transducer cavity 23 under the influence of gravity. Such a bore or channel should hence also be non-horizontal when the gas meter is orientated as intended during use and have an inlet through which condensation water may enter the bore/channel inside the transducer cavity 23, and an outlet located at a lower altitude than said inlet, outside the transducer cavity 23, and preferably inside the gas conduit 3.

According to another exemplary embodiment of the gas meter of the invention (not shown), both the lower and the upper surfaces of the inner wall of the transducer housing are horizontal and the transducer housing is shaped as a cylinder having a perfectly circular cross-section. In this embodiment, the height of the transducer cavity is substantially the same as, or slightly higher than, the height of the measurement chamber. This is advantageous in that the entire gas flow streaming through the measurement chamber is traversed by ultrasonic pulses. In this embodiment, to prevent condensation water from entering the transducer cavities, a channel may be formed in the lower surface of the gas conduit, in the longitudinal direction thereof, just outside the opening leading into the transducer cavity from the measurement chamber. This channel serves as a moat preventing condensation water from entering the transducer cavity from the measurement chamber. The channel is preferably formed as a narrow wedge-shaped groove having zero or a small depth just outside the opening of the transducer cavity, and a depth that increases with the distance from the opening, in the longitudinal direction of the gas conduit, such that condensation water will be pulled away from the opening by gravity.

Referring again to FIG. 3, a heat generator 33 is arranged within the transducer cavity 23 to locally heat the area around the transducer 11A in order to further minimize the risk of liquids penetrating the transducer cavity 23 and filling the air gap 31 surrounding the transducer 11A. The heat generator 33 is thermally coupled to a thermally conductive material 35 substantially surrounding but not contacting the transducer 11A. In this embodiment, the heat generator 33 is a resistive heating film and the thermally conductive material is a metal cylinder surrounding the transducer 11A. The resistive heating film is applied around the metal cylinder, on the side of the metal cylinder not facing the transducer 11A. When heated by the resistive heating film the metal cylinder radiates heat to the air gap 31 such that any liquid potentially penetrating the air gap 31 is evaporated. Arranging the heating means 33 within the transducer cavity 23 to locally heat the area around the transducer 11A is very effective compared to known solutions in which the heating means are arranged outside the transducer housing since, when applying heat from outside the transducer housing, heat is dissipated through the transducer housing and further through the gas conduit instead of reaching the area of interest, resulting in a waste of heating power. In fact, it has been shown that arranging the heat generator 33 inside the transducer cavity 23 instead of outside the transducer housing 16A, the power required by heat generator 33 to keep the air gap 31 free from condensation water is reduced by approximately 50%.

To seal air gaps between the resistive heating film, the metal cylinder and the inner walls 21A, 21B of the transducer housing, the transducer housing 16A comprises through holes 37 through which a sealing paste 39, such as silicon, can be injected.

Although the transducer housing 15A has herein been described with reference to the embodiment of the gas meter illustrated in FIGS. 1A and 1B, it should be appreciated that the transducer housing arrangement illustrated in FIG. 3 may be advantageously used in any gas meter using one or several ultrasound transducers to determine the time of flight of ultrasonic pulses through a fluid that is to be analyzed. For example, the proposed solution of local heating of the area around the transducer 11A is not limited to the gas meter described herein but could be used for any gas meter in which an ultrasound transducer is arranged within a transducer housing, as could the proposed solution of a transducer housing having at least a lower inner wall surface which is inclined relative to the horizontal plane as described above.

It should also be appreciated that although the gas meter has herein been described with reference to embodiments in which two ultrasonic transducers are arranged on opposite sides of the gas conduit, the gas meter might just as well have a single ultrasonic transducer arranged to transmit acoustic pulses through the gas and to receive the pulses after being reflected by the inner wall on the opposite side of the gas conduit, or a reflector element arranged on the opposite side of the gas conduit. Of course, a gas meter using such a single-transducer arrangement may still benefit from the transducer housing design described above with reference to FIG. 3.

The gas meter 1A, 1B described herein is intended for use in a breathing apparatus, such as a ventilator or anaesthesia machine, comprising a tubing system for supplying gas to and from a patient. Preferably, the gas meter is a stand-alone device arranged to be detachably connected inline with the tubing system of the breathing apparatus to form a part thereof. However, the gas meter may also be integrally formed with the tubing system of the breathing apparatus to form a permanent part thereof.

The proposed self-draining gas meter design is particularly advantageous when the gas meter is used in a part of a breathing apparatus tubing system conveying humidified gas, for example gases exhaled by the patient, or gases humidified by a humidifier arranged in the tubing system. However, the gas meter 1A, 1B may be arranged at any location of a breathing circuit at which there is a desire to determine a flow rate or composition of a gas flow, including but not limited to the expiratory line of the breathing circuit conveying exhaled gases away from the patient, the inspiratory line of the breathing circuit conveying breathing gases to the patient, and the common line or lines of the breathing circuit conveying gases both to and from the patient.

Examples of common lines of a breathing circuit in which the gas meter 1A, 1B may be arranged is the common line of a Y-piece normally used in breathing apparatuses to connect the patient with the inspiratory and expiratory lines, and a common line on the distal side of a circle system (i.e. the distal side of the inspiratory and expiratory lines) in which exhalation gases are re-supplied to the patient after removal of carbon dioxide. For example, the proposed gas meter 1A, 1B is advantageously used in the common line on the distal side of a circle system of volume reflector type, as described in co-pending international patent application PCT/EP2009/055789, in which case the gas sensor unit denoted by reference numeral 640 in FIGS. 1 and 2 is advantageously implemented in form of the gas meter 1A, 1B described herein.

Although modifications and changes may be suggested by those skilled in the art, it is the intention of the inventors to embody within the patent warranted heron all changes and modifications as reasonably and properly come within the scope of their contribution to the art.

We claim as our invention:

1. A gas meter for ultrasound measurements in a breathing apparatus, comprising:
    a gas conduit having an inner wall defining an inlet in a first end of the gas conduit and an outlet in a second end of the gas conduit, said inner wall having a lower inner wall surface forming a bottom, relative to a direction of gravity, of an interior of said gas conduit;
    an ultrasound transducer arrangement configured to measure the speed of sound in a gas flowing through a part of said gas conduit forming a measurement chamber;
    said lower inner wall surface of the inner wall being inclined downwardly in said direction of gravity, relative to a horizontal plane in a longitudinal direction of the gas conduit, at both sides of the measurement chamber with a highest part of said lower inner wall surface being situated in said measurement chamber, causing condensation water to be pulled away from the measurement chamber by gravity.

2. Gas meter according to claim 1, wherein said inner wall comprises an upper inner wall surface that is inclined downwardly relative to the horizontal plane in the longitudinal direction of the gas conduit, at both sides of the measurement chamber.

3. Gas meter according to claim 1, wherein the lower inner wall surface is upwardly convexly curved toward the horizontal plane.

4. Gas meter according to claim 1, wherein the lower inner wall surface has a substantially constant, positive slope from the inlet to the highest part in the measurement chamber and a substantially constant, negative slope from the highest part in the measurement chamber to the outlet.

5. Gas meter according to claim 1, wherein the inlet and the outlet are situated in said horizontal plane, and wherein the first end and the second end of the gas conduit each comprise a connection configured to allow the gas conduit to be connected in between two horizontal and longitudinally aligned gas conduits.

6. Gas meter according to claim 1, wherein the ultrasound transducer arrangement comprises at least one ultrasound transducer in a transducer housing protruding from the gas conduit, the transducer housing having an inner wall forming a transducer cavity having a closed end at which the transducer is arranged and an open end forming an opening into the measurement chamber, through which opening the transducer is arranged to transmit and/or receive ultrasonic pulses.

7. Gas meter according to claim 6, wherein at least a lower surface of the inner wall of the transducer housing is inclined upwardly relative to the horizontal plane from the open end of the transducer cavity toward the closed end.

8. Gas meter according to claim 6, wherein the transducer cavity comprises a heat generator that locally heats an area around the transducer to keep the area free from condensation water.

9. Gas meter according to claim 8, wherein the transducer cavity comprises a thermally conductive material which is thermally coupled to the heat generator to participate in the local heating of the area around the transducer.

10. Gas meter according to claim 9, wherein the transducer cavity has a substantially circular cross section, the thermally conductive material being a metal cylinder surrounding the transducer, and the heat generator is a resistive heating film arranged between the metal cylinder and the inner wall of the transducer housing.

11. Gas meter according to claim 10, wherein the transducer housing comprises at least one through hole for allowing a sealing paste to be injected into the transducer cavity to seal air gaps between the resistive heating film, the metal cylinder, and/or the inner wall of the transducer housing.

12. Gas meter according to claim 1 wherein said highest part of said lower inner wall surface is situated at a longitudinal center of said gas conduit, midway between said inlet and said outlet.

13. Gas meter according to claim 1 wherein said highest part of said lower inner wall surface is in said horizontal plane.

* * * * *